US008444925B2

(12) United States Patent
Baba

(10) Patent No.: US 8,444,925 B2

(45) **Date of Patent: *May 21, 2013**

(54) LIGNOCELLULOSIC BIOMASS SACCHARIFICATION PRE-TREATMENT DEVICE

(75) Inventor: Tsuyoshi Baba, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 62 days.
This patent is subject to a terminal disclaimer.

(21) Appl. No.: 13/139,251

(22) PCT Filed: Nov. 25, 2009

(86) PCT No.: PCT/JP2009/006353

§ 371 (c)(1), (2), (4) Date: Jun. 10, 2011

(87) PCT Pub. No.: WO2010/070817
PCT Pub. Date: Jun. 24, 2010

(65) Prior Publication Data

US 2011/0239685 A1 Oct. 6, 2011

(30) Foreign Application Priority Data

Dec. 16, 2008 (JP) ................................ 2008-319429

(51) Int. Cl.

| | |
|---|---|
| ***B01J 19/00*** | (2006.01) |
| *B01J 8/00* | (2006.01) |
| *B01J 10/00* | (2006.01) |
| *C01C 1/00* | (2006.01) |
| *C12P 19/00* | (2006.01) |
| *C12P 19/02* | (2006.01) |

(52) U.S. Cl.
USPC ........... 422/198; 422/129; 422/148; 422/187; 435/72; 435/105

(58) Field of Classification Search
USPC .... 422/129, 148, 187, 198; 62/324.1; 435/41, 435/72, 105; 426/69, 665, 474–476, 615, 426/635, 807; 162/1, 17, 29, 70, 239, 232, 162/233, 250
See application file for complete search history.

(56) References Cited

U.S. PATENT DOCUMENTS 7,144,552 B1 12/2006 Fukuizumi et al.
2009/0098251 A1* 4/2009 Rajagopalan et al. .......... 426/69
2012/0012266 A1* 1/2012 Baba et al. .................... 162/239

FOREIGN PATENT DOCUMENTS

JP 4-80570 A 3/1992
JP 2001-179063 A 7/2001
JP 2005-232453 A 9/2005
JP 2005-288320 A 10/2005
JP 2007-275889 A 10/2007

OTHER PUBLICATIONS

Teyouri et al., Optimization of the ammonia fiber explosion (AFEX) treatment parameters for enzymatic hydrolysis of corn stover, Feb. 24, 2005, Bioresource Technology 96, 2014-2018.*
Tae Hyun Kim et al., "Pretreatment and fractionation of corn stover by ammonia recycle percolation process", Bioresource Technology, 2005, vol. 96, p. 2007-2013.
Elizabeth (Newton) Sendich et al., "Recent process improvements for the ammonia fiber expansion (AFEX) process and resulting reductions in minimum ethanol selling price", Bioresource Technology, Apr. 8, 2008, vol. 99, p. 8429-8435.

* cited by examiner

*Primary Examiner* — Jill Warden
*Assistant Examiner* — Natasha Young
(74) *Attorney, Agent, or Firm* — Arent Fox LLP

(57) ABSTRACT

A lignocellulosic biomass saccharification pre-treatment device for easily recovering ammonia water to be used in a pre-treatment for saccharification of a lignocellulosic biomass and recycle use. The device has a mixing unit 2 mixing lignocellulosic biomass and ammonia, a heating unit 3 heating the mixture, a separation unit 4 separating ammonia gas from the mixture to obtain a biomass-water mixture, and a transfer unit 6 transferring the biomass-water mixture to a later process. An ammonia water supply unit 8 supplies ammonia water to the mixing means 2. An ammonia recovery unit 20 recovers ammonia gas as ammonia water. A heat-of-dissolution recovery unit 24 recovers heat-of-dissolution generated when ammonia gas is dissolved in water. A heat pump unit 30 generates heat to be supplied to the heating unit 3 using at least the heat-of-dissolution as a heat source.

5 Claims, 2 Drawing Sheets

LIGNOCELLULOSIC BIOMASS SACCHARIFICATION PRE-TREATMENT DEVICE

CROSS-REFERENCE TO RELATED APPLICATION

This application is a National Stage entry of International Application No. PCT/JP2009/006353, filed Nov. 25, 2009, which claims priority to Japanese Patent Application No. 2008-319429 filed Dec. 16, 2008, the disclosure of the prior applications are incorporated in its entirety by reference.

TECHNICAL FIELD

The present invention relates to a saccharification pre-treatment device for use in saccharifying lignocellulosic biomass as a raw material for producing bioethanol.

BACKGROUND ART

Recently, reduction of emissions of carbon-dioxide, which is considered as contribution to global warming prevention, has been required and thus use of a blended fuel of liquid hydrocarbon such as gasoline and ethanol as motor fuel has been investigated. As the ethanol, a bioethanol obtained by fermentation of a plant substance such as sugar cane and corn can be used. Since the plant substance used as a raw material itself has already absorbed carbon dioxide by photosynthesis, if ethanol obtained from such a plant substance is burned, the discharge amount of carbon dioxide is equal to the amount of carbon dioxide absorbed by the plant itself. In short, carbon dioxide emission on the whole theoretically becomes zero. More specifically, a so-called carbon neutral effect can be obtained. Therefore, if bioethanol is used in place of liquid hydrocarbon such as gasoline, carbon-dioxide emission can be reduced by the amount of bioethanol.

However, the sugar cane, corn and the like should be used fundamentally as food. If they are used as a raw material for bioethanol in a large amount, the amount of them supplied as food is reduced. This is a problem.

Therefore, a technique for producing ethanol using nonedible lignocellulosic biomass in place of a plant substance such as sugar cane and corn has been investigated. The lignocellulosic biomass contains cellulose. If the cellulose is decomposed by enzymatic saccharification into glucose and the obtained glucose is fermented, bioethanol can be obtained. Examples of the lignocellulosic biomass include wood, rice straw, wheat straw, bagasse, bamboo, pulp and waste materials (e.g., used paper) produced from these.

However, lignocellulose contains hemicellulose and lignin other than cellulose as major components. Usually cellulose and hemicellulose are tightly bound to lignin. It is difficult to apply an enzymatic saccharification reaction directly to the cellulose. Accordingly, when the cellulose is subjected to an enzymatic saccharification reaction, lignin is desirably removed in advance.

For removing lignin from lignocellulose, a saccharification pre-treatment device is known, in which lignocellulosic biomass is mixed with liquid ammonia and then the pressure is rapidly reduced to remove lignin from the lignocellulosic biomass (see, for example, Patent Literature 1).

In the conventional saccharification pre-treatment device, first lignocellulosic biomass is mixed with liquid ammonia by mixing means and the resultant biomass-ammonia mixture is heated by heating unit. Next, the biomass-ammonia mixture heated is pressurized and compressed by pressurization means so as for ammonia not to evaporate and discharged by discharge means.

If treated in this manner, the biomass-ammonia mixture is rapidly reduced in pressure with the progress of discharge and liquid ammonia is evaporated; at the same time, explosively expanded. As a result, the biomass is rapidly expanded to remove lignin bound to cellulose and hemicellulose of the biomass.

However, in the conventional saccharification pre-treatment device, since the biomass-ammonia mixture must be treated at a high temperature and a high pressure, it is difficult to treat the mixture in a continuous manner. This is a disadvantage. In addition, in the conventional saccharification pre-treatment device, in order to recover ammonia gas separated from the biomass-ammonia mixture and reuse it as liquid ammonia, the ammonia gas must be pressurized to about 2 MPa. Cost inevitably increases. This is another disadvantage.

To overcome the disadvantages, it is considered to use ammonia water in place of liquid ammonia. When ammonia water is used, lignocellulosic biomass is mixed with ammonia water to provide a biomass-ammonia mixture. Then, if the biomass-ammonia mixture is heated and boiled, the biomass expands by the expansion effect of the ammonia water by boiling; at the same time, the mixture is treated with alkali of the ammonia water to remove lignin.

Accordingly, when ammonia water is used, lignin can be removed by a boiling treatment without applying pressurization/compression. Therefore, the biomass can be easily treated in a continuous manner and cellulose of the biomass can be subjected to an enzymatic saccharification reaction without being inhibited by lignin.

Furthermore, when ammonia water is used, ammonia gas evaporated from the biomass-ammonia mixture boiled can be dissolved in water and recovered as ammonia water, and put in recycle use.

However, when ammonia gas is dissolved in water, heat of dissolution generates. If the temperature of ammonia water is increased by the heat of dissolution, the solubility of ammonia reduces. This is a problem and an improvement thereof is desired.

Citation List

Patent Literature

Patent Literature 1: Japanese Patent Laid-Open No. 2005-232453

SUMMARY OF INVENTION

Technical Problem

The present invention was made in the aforementioned circumstances. An object of the invention is to provide a lignocellulosic biomass saccharification pre-treatment device in the case where ammonia water is used in saccharification pre-treatment of lignocellulosic biomass which is capable of easily recovering the ammonia water for recycle use.

Solution to Problem

To attain the object, the present invention provides a lignocellulosic biomass saccharification pre-treatment device having a mixing unit which mixes lignocellulosic biomass and ammonia, a heating unit which heats a biomass-ammonia mixture obtained by the mixing means, a separation unit which separates ammonia gas from the biomass-ammonia mixture heated by the heating unit to obtain a biomass-water mixture, and a transfer unit which transfers the biomass-water mixture separated by the separation unit to a later process, the device which has an ammonia water supply unit which supplies ammonia water to the mixing means, an ammonia recovery unit which recovers ammonia gas separated by the separation unit as ammonia water by dissolving the ammonia gas in water, a heat-of-dissolution recovery unit which recovers heat-of dissolution generated when ammonia gas is dissolved in water by the ammonia recovery unit, and a heat pump unit which generates heat to be supplied to the heating unit by using at least the heat-of-dissolution recovered by the heat-of-dissolution recovery unit as a heat source.

In the lignocellulosic biomass saccharification pre-treatment device of the present invention, the lignocellulosic biomass is first mixed, in the mixing means, with ammonia water supplied by the ammonia water supply means to provide a biomass-ammonia mixture. Next, the biomass-ammonia mixture is heated by the heating unit and boiled. At this time, the biomass is expanded by the ammonia water and simultaneously treated with alkali to remove lignin.

Next, the biomass-ammonia mixture is supplied to the separation unit at which ammonia gas evaporated by boiling of the biomass-ammonia mixture is separated to provide a biomass-water mixture. Subsequently, the biomass-water mixture is transferred to a later process by the transfer means.

In contrast, the ammonia gas separated by the separation unit is dissolved in water by the ammonia recovery unit and recovered as ammonia water. At this time, i.e., when the ammonia gas is dissolved, heat of dissolution is generated. As a result, the temperature of the ammonia water increases and the solubility of ammonia decreases. It is concerned that recovery of ammonia gas becomes difficult.

Then, in the lignocellulosic biomass saccharification pre-treatment device of the present invention, heat-of-dissolution recovery unit is provided to recover the heat-of-dissolution. The heat-of-dissolution is used as a heat source for the heat pump. The heat generated by the heat pump is supplied to the heating unit.

Thus, according to the lignocellulosic biomass saccharification pre-treatment device of the present invention, lignin can be removed by applying a boiling treatment to the biomass with ammonia water without requiring pressurization/compression. Furthermore, according to the lignocellulosic biomass saccharification pre-treatment device of the present invention, the biomass can be easily treated in a continuous manner.

Furthermore, according to the lignocellulosic biomass saccharification pre-treatment device of the present invention, ammonia gas evaporated as a result of a boiling treatment of the biomass-ammonia mixture is dissolved in water to obtain ammonia water. Accordingly, an apparatus or the like for liquefying ammonia gas by pressurization/compression is not required.

Furthermore, according to the lignocellulosic biomass saccharification pre-treatment device of the present invention, heat-of-dissolution generated in dissolving the ammonia gas in water is recovered by the heat-of-dissolution recovery unit. Accordingly, ammonium gas can be easily recovered while preventing an increase in temperature of the ammonia water. Furthermore, by supplying heat generated by the heat pump using the heat-of-dissolution as a heat source to the heating unit, energy efficiency can be increased.

If ammonia remains in the biomass-water mixture to be transferred to a later process by the transfer means, since ammonia is alkali, there is a possibility that enzymatic saccharification of cellulose to be performed in the later process may be inhibited. Then, the lignocellulosic biomass saccharification pre-treatment device of the present invention preferably has a reheating unit which reheats a biomass-ammonia mixture heated by the heating unit and an evaporating unit which evaporates ammonia gas from the biomass-ammonia mixture heated by the reheating unit between the heating unit and the separation unit. By reheating the biomass-ammonia mixture by the reheating unit so that ammonia gas is evaporated by the evaporating means, ammonia gas can be separated in the separation unit without fail. Accordingly, it is possible to prevent ammonia from remaining in the biomass-water mixture.

Furthermore, the lignocellulosic biomass saccharification pre-treatment device of the present invention further has a first heat recovery unit which recovers heat from ammonia gas separated by the separation unit and a second heat recovery unit which recovers heat from the biomass-water mixture separated by the separation unit, in which the heat pump unit preferably generates heat to be supplied to the heating unit and the reheating unit using the heat-of-dissolution recovered by the heat-of-dissolution recovery unit and the heat recovered by the first and second heat recovery unit as a heat source.

In this manner, extra heat of the ammonia gas and the biomass-water mixture can be recovered and the energy efficiency of the device can be further increased. Furthermore, according to the first heat recovery unit, dissolution of the ammonia gas in water can be facilitated by recovering extra heat from the ammonia gas. Furthermore, according to the second heat recovery unit, the temperature of the biomass-water mixture can be regulated to be suitable for the enzymatic saccharification treatment by recovering extra heat from the biomass-water mixture.

Furthermore, the lignocellulosic biomass saccharification pre-treatment device of the present invention further has a third heat recovery unit which recovers heat in the air, in which the heat pump unit preferably has a first heat pump for generating heat to be supplied to the heating unit using heat-of-dissolution recovered by the heat-of-dissolution recovery unit and heat recovered by the third heat recovery unit as a heat source and a second heat pump for generating heat to be supplied to the reheating unit using the heat generated by the first heat pump as a heat source.

In this manner, supply of heat to the heating unit and supply of heat to the reheating unit are each independently performed and appropriate amount of heat can be supplied to each of them.

Furthermore, the lignocellulosic biomass saccharification pre-treatment device of the present invention preferably has a storage unit which stores the biomass-ammonia mixture heated by the heating unit. According to the storage unit, since ammonia can be sufficiently expanded relative to the biomass-ammonia mixture heated by the heating unit, lignin can be removed by an alkali treatment without fail.

DESCRIPTION OF EMBODIMENT

Next, the invention according to the embodiment will be more specifically described with reference to the accompanying drawings.

Figure 1:
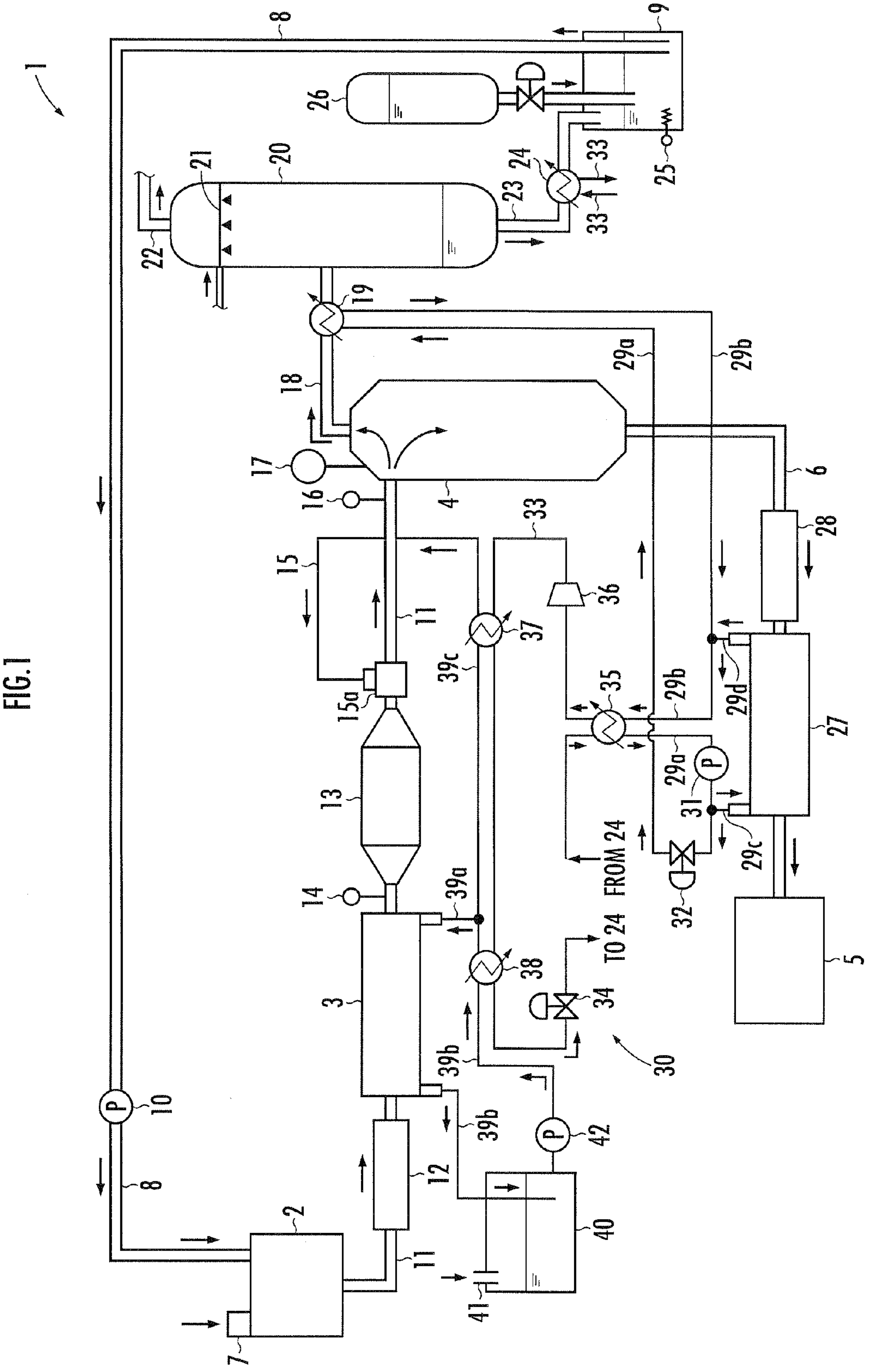
FIG. 1 is a configuration diagram of the system of a lignocellulosic biomass saccharification pre-treatment device of the present invention.

As shown in FIG. 1, a lignocellulosic biomass saccharification pre-treatment device 1 according to the embodiment has a mixer 2 for mixing lignocellulosic biomass (hereinafter, sometimes simply referred to as biomass) and ammonia to obtain slurry having the biomass and ammonia mixed therein, a first multitubular heat exchanger 3 for heating the slurry obtained in the mixer 2, a separation tower 4 for separating ammonia gas from the slurry heated by the first multitubular heat exchanger 3 to obtain a biomass-water mixture and a transfer pipe 6 for discharging the biomass-water mixture separated by the separation tower 4 and transferring it to a later process 5.

The mixer 2 has an inlet 7 at the top for introducing the biomass and also has an ammonia water supply pipe 8 connected for supplying ammonia water to be mixed with the biomass. The end of the ammonia water supply pipe 8 on the upstream side is connected to an ammonia tank 9 and has a pump 10 in the middle.

In the lower portion of the mixer 2, a slurry pipe 11 is provided for discharging the slurry. The slurry pipe 11 is connected to the separation tower 4 via the first multitubular heat exchanger 3. The slurry pipe 11 has a slurry pump 12 for feeding the slurry to the first multitubular heat exchanger 3 on the upstream side of the first multitubular heat exchanger 3 and also has a hold tank 13 for storing the slurry on the downstream side of the first multitubular heat exchanger 3. Furthermore, the slurry pipe 11 has a first temperature sensor 14 for detecting the temperature of the slurry at the outlet of the first multitubular heat exchanger 3, a vapor pipe 15 connected to the hold tank 13 at the downstream side thereof and a second temperature sensor 16 for detecting the temperature of the slurry at the inlet of the separation tower 4. The vapor pipe 15 is connected to the slurry pipe 11 via an open/shut valve 15*a*.

In the separation tower 4, the slurry pipe 11 is connected to the upper portion thereof and the transfer pipe 6 is provided to the bottom. Furthermore, to the top portion thereof, a pressure sensor 17 for detecting the pressure within the separation tower 4 and an ammonia gas pipe 18 for discharging separated ammonia gas are provided. The ammonia gas pipe 18 is connected to an absorption tower 20 via the first heat exchanger 19.

The absorption tower 20 has a showering unit 21 above the portion at which the ammonia gas pipe 18 is connected. The ammonia gas introduced through the ammonia gas pipe 18 is absorbed to the water showered by the showering unit 21 to obtain ammonia water, which is stored in the bottom of the absorption tower 20.

The absorption tower 20 has an air vent pipe 22 at the top and an ammonia water discharge pipe 23 is provided to the bottom for discharging the ammonia water. The end of the ammonia water discharge pipe 23 on the downstream side is connected to the ammonia tank 9 via a second heat exchanger 24.

The ammonia tank 9 has an ammonia concentration sensor 25 for detecting the concentration of the ammonia water stored therein and a concentrated ammonia water supply unit 26. The concentrated ammonia water supply unit 26 supplies concentrated ammonia water to the ammonia tank 9 depending upon the concentration of ammonia water detected by the ammonia concentration sensor 25.

The transfer pipe 6 is connected to the later process 5 via a second multitubular heat exchanger 27. The transfer pipe 6 has a slurry pump 28 on the upstream side of the second multitubular heat exchanger 27, for feeding the biomass-water mixture to the second multitubular heat exchanger 27.

The first heat exchanger 19 provided in the middle of the ammonia gas pipe 18 is connected to a heat pump 30 by way of a first heat medium pipe 29*a* and a second heat medium pipe 29*b*. The first heat medium pipe 29*a* connects the secondary side of the heat pump 30 and the primary side of the first heat exchanger 19, whereas the second heat medium pipe 29*b* connects the secondary side of the first heat exchanger 19 and the primary side of the heat pump 30. Note that the same heat medium such as water and ethylene glycol is passed through the first heat medium pipe 29*a* and the second heat medium pipe 29*b*.

Furthermore, the first heat medium pipe 29*a* has a heat medium pump 31. From the downstream side of the heat medium pump 31, a third heat medium pipe 29*c* is diverged, which is connected to the primary side of the second multitubular heat exchanger 27. A flow-rate regulation valve 32 is provided on the downstream side of the junction point of the third heat medium pipe 29*c*. Onto the secondary side of the second multitubular heat exchanger 27, a fourth heat medium pipe 29*d* is provided. The fourth heat medium pipe 29*d* merges into the second heat medium pipe 29*b* in the middle.

The heat pump 30 has a circulation pipe 33 for circulating a heat medium such as carbon dioxide. In the middle of the circulation pipe 33, an expansion valve 34, the second heat exchanger 24, a third heat exchanger 35, a compressor 36, a fourth heat exchanger 37 and a fifth heat exchanger 38 are provided. The first heat exchanger 19 provided in the middle of the ammonia gas pipe 17 is connected to the third heat exchanger 35 by way of the first heat medium pipe 29*a* and the second heat medium pipe 29*b*.

Whereas, the first multitubular heat exchanger 3 is connected to the fifth heat exchanger 38 of the heat pump 30 by way of a first water pipe 39*a* and a second water pipe 39*b*. The first water pipe 39*a* connects the secondary side of the fifth heat exchanger 38 and the primary side of the first multitubular heat exchanger 3, whereas the second water pipe 39*b* connects the secondary side of the first multitubular heat exchanger 3 and the primary side of the fifth heat exchanger 38.

From the first water pipe 39*a*, a third water pipe 39*c* is diverged. The third water pipe 39*c* is connected to the primary side of the fourth heat exchanger 37. To the secondary side of the fourth heat exchanger 37, the vapor pipe 15 is connected.

The amount of water circulated to the first multitubular heat exchanger 3 through the first water pipe 39*a* and the second water pipe 39*b* is reduced by the amount of water passing through the third water pipe 39*c*. Accordingly, a water tank 40 is provided in the middle of the second water pipe 39*b* to supplement water to pass through the third water pipe 39*c*. The water tank 40 has a supplemental water pipe 41 for supplying required amount of water from outside. Furthermore, the second water pipe 39*b* has a pump 42 on the downstream side of the water tank 40.

Figure 2:
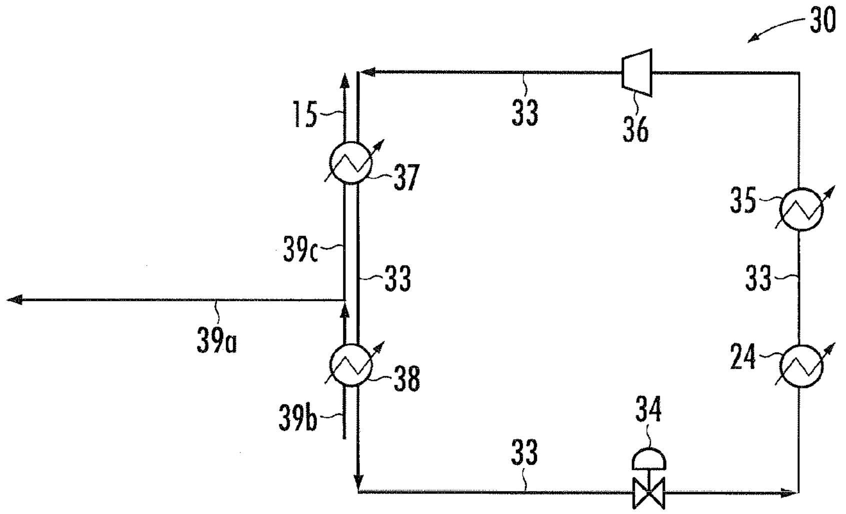
FIG. 2 is a view of schematically illustrating an example of the heat pump line shown in FIG. 1.

Note that the schematic view of the line of the heat pump 30 is shown in FIG. 2.

Next, referring to FIG. 1 and FIG. 2, how to operate the lignocellulosic biomass saccharification pre-treatment device 1 of the embodiment will be described.

In the lignocellulosic biomass saccharification pre-treatment device 1 of the embodiment, first the biomass is introduced from the inlet 7 to the mixer 2. The biomass is, for example, naturally dried rice straw having a water content of about 10 wt %. The biomass is pulverized into pieces of about 3 mm in length by a cutter mill (not shown) and then further pulverized by a dry-system blade mill (not shown) into powder having a cumulative 50% particle size of 140 μm. The biomass is supplied by, for example, a screw feeder (not shown) to the biomass inlet 7.

Next, ammonia water in the ammonia tank 9 is supplied to the mixer 2 by means of the pump 10 through the ammonia water supply pipe 8. At this time, the concentration of the ammonia water to be supplied into the mixer 2 has been regulated to, for example, 28.6 wt %. The biomass and the ammonia water are supplied, for example, at a flow rate of 12 kg/hour and 48 kg/hour respectively to the mixer 2 such that they satisfy a weight ratio of, for example, 1:4.

Next, the biomass supplied to the mixer 2 is mixed with the ammonia water by the mixer 2 to prepare slurry. The slurry prepared in the mixer 2 is fed to the first multitubular heat exchanger 3 so as to satisfy a flow rate of, for example, 60 kg/hour, by means of the slurry pump 12 through the slurry pipe 11. The first multitubular heat exchanger 3 heats the slurry by use of the hot water having a temperature of about 85° C. which is supplied through the first water pipe 39*a*. The hot water is heated to the above temperature by the fifth heat exchanger 38 of the heat pump 30. At this time, the temperature of the slurry detected at the outlet of the first multitubular heat exchanger 3 by the first temperature sensor 14 is about 65° C.

Next, the slurry heated by the first multitubular heat exchanger 3 is stored in the hold tank 13 for a predetermined time. During the storage, the biomass is expanded by the ammonia water; at the same time, treated with alkali to remove lignin bound to cellulose and hemicellulose in the biomass.

Next, the slurry is supplied to the separation tower 4 through the slurry pipe 11. At this time, the slurry is reheated such that the temperature of the slurry detected by the second temperature sensor 16 at the end of the slurry pipe 11 becomes about 100° C. The reheating is performed by water vapor supplied from the vapor pipe 15 via the open/shut valve 15*a* and heated to about 135° C. The water vapor is heated to the temperature mentioned above by the fourth heat exchanger 37 of the heat pump 30.

As a result, from the slurry within the slurry pipe 11 between the open/shut valve 15*a* and the separation tower 4, ammonia is vaporized. When the slurry is supplied to the separation tower 4, the ammonia gas evaporated is separated from the slurry.

The ammonia gas is supplied to the absorption tower 20 through the ammonia gas pipe 18 and via the first heat exchanger 19. The ammonia gas supplied to the absorption tower 20 is absorbed by the water showed from the showering unit 21 and stored as ammonia water at the bottom of the absorption tower 20. The showing of water by the showering unit 21 is performed in a water amount of 35.2 kg/hour.

At this time, since extra heat of the ammonia gas has been recovered by the first heat exchanger 19, the ammonia gas is susceptible to being absorbed by the water showered from the showering unit 21. However, when the ammonia gas is dissolved in water, heat-of-dissolution generates. If the temperature of the ammonia water is increased by the heat-of-dissolution, there is a concern that ammonia may not be sufficiently dissolved in the water.

Then, in the embodiment, when the ammonia water stored at the bottom of the absorption tower 20 is returned to the ammonia tank 9 through the ammonia water discharge pipe 23, the heat-of-dissolution is recovered by the second heat exchanger 24 provided to the ammonia water discharge pipe 23. As a result, in the absorption tower 20, a sufficient amount of ammonia gas is absorbed by the water showered from the showering unit 21 and recovered as ammonia water.

Furthermore, in the ammonia tank 9, the ammonia concentration of the ammonia water stored therein is detected by the ammonia concentration sensor 25. Subsequently, depending upon the ammonia concentration detected, the concentrated ammonia water supply unit 26 supplies concentrated ammonia water to the ammonia tank 9. As a result, the ammonia water in the ammonia tank 9 is regulated to an ammonia concentration of, for example, 28.6 wt % and supplied to the mixer 2 through the ammonia water supply pipe 8.

The heat herein recovered by the first heat exchanger 19 and the second heat exchanger 24 is used as a heat source for the heat pump 30 described later.

In the meantime, the slurry, from which ammonia gas is separated by the separation tower 4, is transferred as a biomass-water mixture solution by the slurry pump 28 to the later process 5 through the transfer pipe 6. At this time, ammonia in the slurry is evaporated within the slurry pipe 11 by heating the slurry by the water vapor to obtain ammonia gas in the separation tower 4. In this mariner, ammonia is completely separated from the slurry. As a result, the biomass-water mixture solution does not substantially contain ammonia.

The later process 5 is a process of applying an enzymatic saccharification treatment to cellulose contained in the biomass by, for example, supplying predetermined amounts of water and saccharification enzyme to the biomass-water mixture. From the biomass-water mixture, extra heat is recovered by the second multitubular heat exchanger 27 provided to the transfer pipe 6. The heat recovered by the second multitubular heat exchanger 27 is used as a heat source of the heat pump 30 described later.

In the heat pump 30 shown in FIG. 2, for example, carbon dioxide is used as a heat medium. In this case, in the heat pump 30, carbon dioxide circulating through the circulation pipe 33 is expanded by the expansion valve 34 so as to have a pressure of 3 MPa and a temperature of −5.5° C., and supplied to the second heat exchanger 24. As a result, the carbon dioxide absorbs heat-of-dissolution of the ammonia gas in the second heat exchanger 24 and increases in temperature to about +5° C.

Next, the carbon dioxide passed through the second heat exchanger 24 is further supplied to the third heat exchanger 35. In the third heat exchanger 35, a heat medium such as water and ethylene glycol circulating through the first heat medium pipe 29*a* and the second heat medium pipe 29*b* has been supplied. The carbon dioxide exchanges heat with the heat medium, and heated to a temperature of about +15° C. at a pressure of 3 MPa.

The carbon dioxide passing through the third heat exchanger 35 is then supplied to the compressor 36 and compressed therein to go into a supercritical state (a pressure of 130 MPa and a temperature of 138° C.). Next, the carbon dioxide exchanges heat with hot water supplied from the third water pipe 39*c* at the fourth heat exchanger 37 to change the water into water vapor having a temperature of 130° C. Thereafter, the carbon dioxide exchanges heat with the water supplied from the second water pipe 39*b* at the fifth heat exchanger 38 located further downstream to change the water to hot water having a temperature of 80° C. The carbon dioxide having a pressure of 13 MPa and a temperature of 40° C. is circulated to the expansion valve 34.

At this time, the heat medium such water and ethylene glycol discharged from the secondary side of the third heat exchanger 35 is introduced by the heat medium pump 31 into the primary side of the first heat exchanger 19 through the first heat medium pipe 29*a*. Furthermore, the heat medium is introduced into the primary side of the second multitubular heat exchanger 27 through the third heat medium pipe 29*c* diverged from the first heat medium pipe 29*a*. The partition ratio of the heat medium flowing through the first heat medium pipe 29*a* to the third heat medium pipe 29*c* is regulated by the flow-rate regulation valve 32. Next, the heat medium recovers extra heat of the ammonia gas and the biomass-water mixture and thereafter is discharged from the secondary side of the first heat exchanger 19 and the second multitubular heat exchanger 27. Thereafter, the heat medium passes through the second heat medium pipe 29*b* and the fourth heat medium pipe 29*d* and is introduced from the primary side of the third heat exchanger 35.

Furthermore, water vapor having a temperature of 130° C. obtained by the fourth heat exchanger 37 is supplied to the slurry pipe 11 through the vapor pipe 15 and used for reheating the slurry. Furthermore, the hot water having a temperature of 80° C. obtained by the fifth heat exchanger 38 is supplied to the primary side of the first multitubular heat exchanger 3 through the first water pipe 39*a* and used for heating the slurry. After heating the slurry, the hot water is discharged from the secondary side of the first multitubular heat exchanger 3 through the second water pipe 39*b*, supplemented with water for compensating a shortage in the water tank 40 and supplied to the fifth heat exchanger 38 via the pump 42.

Note that since the third water pipe 39*c* is diverged from the first water pipe 39*a*, the hot water supplied from the third water pipe 39*c* to the fourth heat exchanger 37 is previously heated by the fifth heat exchanger 38. Furthermore, the amount of water supplied in the water tank 40 to the second water pipe 39*b* to compensate for the shortage corresponds to the amount of water supplied from the third water pipe 39*c* to the fourth heat exchanger 37.

Next, referring to FIG. 3, a modified example of the heat pump 30 will be described. The heat pump 30 shown in FIG. 3 has two types of heat medium circulation systems, a first circulation pipe 33 and a second circulation pipe 43.

In the second circulation pipe 43, for example, trifluoroethanol (hereinafter, simply referred to as TFE) is circulated as a heat medium. The second circulation pipe 43 has an expansion valve 46, a fourth heat exchanger 37, a compressor 44 and a sixth heat exchanger 45 in the middle.

In contrast, in the first circulation pipe 33, for example, carbon dioxide is circulated as a heat medium. The first circulation pipe 33 has a third heat exchanger 35*a* for recovering heat in the air in place of the third heat exchanger 35 shown in the configuration diagrams of FIG. 1 and FIG. 2. Furthermore, the first circulation pipe 33 has a switching valve 48 on the downstream side of the compressor 36, a switching valve 49 on the upstream side of the expansion valve 34, a bypass pipe 33*a* connecting the switching valves 48 and 49 and a seventh heat exchanger 50 provided in the middle of the bypass pipe 33*a*. Except for the components described above, the first circulation pipe 33 is constituted in the same manner as that of the first circulation pipe 33 shown in FIG. 1 and FIG. 2.

Note that, to the seventh heat exchanger 50, the first water pipe 39*a* and the second water pipe 39*b* are connected. In the middle of the first water pipe 39*a*, a keep-warm tank (not shown) is provided. Furthermore, from the secondary side of the fifth heat exchanger 38, a hot water pipe 47 is led outside out and is connected to the sixth heat exchanger 45. From the secondary side of the sixth heat exchanger 45, the vapor pipe 15 is led outside.

Next, how to operate the heat pump 30 shown in FIG. 3 will be described.

Figure 3:
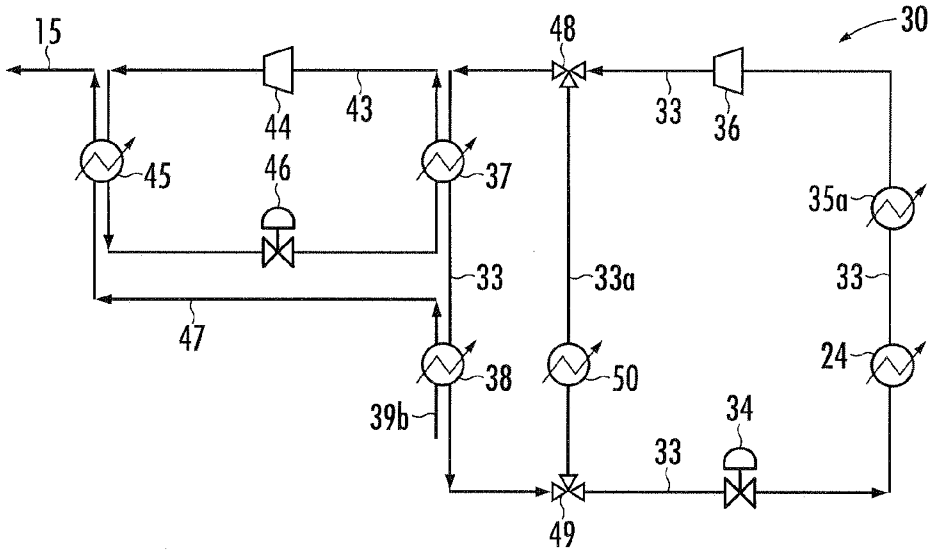
FIG. 3 is a view of schematically illustrating a modified example of the heat pump line shown in FIG. 1.

The heat pump 30 shown in FIG. 3, heating of the slurry in the first multitubular heat exchanger 3 and generation of water vapor for use in reheating the slurry and supplied through the vapor pipe 15, are independently performed by operating the switching valves 48 and 49 of the first circulation pipe 33.

First, when the slurry is heated in the first multitubular heat exchanger 3, the switching valves 48 and 49 are operated to allow carbon dioxide as a heat medium to flow through the bypass pipe 33*a*. Carbon dioxide does not flow through the fourth heat exchanger 37 and the fifth heat exchanger 38. At this time, in the heat pump 30, carbon dioxide circulating through the circulation pipe 33 is first expanded by the expansion valve 34 so as to have a pressure of 3 MPa and a temperature of −5.5° C. and supplied to the second heat exchanger 24. As a result, carbon dioxide absorbs heat-of-dissolution of the ammonia gas in the second heat exchanger 24 and increases in temperature to about +5° C.

Next, the carbon dioxide passed through the second heat exchanger 24 is further supplied to the third heat exchanger 35*a*. In the third heat exchanger 35*a*, the carbon dioxide exchanges heat with the air and is further heated to about +15° C. at a pressure of 3 MPa.

The carbon dioxide passed through the third heat exchanger 35 is then supplied to the compressor 36 and compressed therein to go into a supercritical state (a pressure of 130 MPa and a temperature of 138° C.). Thereafter, carbon dioxide is passed through the bypass pipe 33*a* to exchange heat with the water supplied from the second water pipe 39*b* at the seventh heat exchanger 50 to change the water to hot water having a temperature of 80° C. The carbon dioxide having a pressure of 13 MPa and a temperature of 40° C. is circulated to the expansion valve 34.

The hot water having a temperature of 80° C. obtained in the seventh heat exchanger 50 is supplied to the primary side of the first multitubular heat exchanger 3 through the first water pipe 39*a* and used for heating the slurry. At this time, the first water pipe 39*a* has a keep-warm tank (not shown) in the middle to store the hot water.

In the heat pump 30 shown in FIG. 3, the slurry is heated as described above. In the heat pump 30, when the hold tank 13 is filled with the slurry, water vapor to be supplied through the vapor pipe 15 is generated by operating the switching valves 48 and 49. The water vapor is used for reheating the slurry. At this time, carbon dioxide serving as a heat medium is passed through the fourth heat exchanger 37 and the fifth heat exchanger 38 but does not pass though the bypass pipe 33*a*.

When the water vapor is generated, in the heat pump 30, the carbon dioxide of the supercritical state (a pressure of 130 MPa and a temperature of 138° C.) obtained by the compressor 36 as mentioned above is first supplied to the fourth heat exchanger 37 at which the water vapor exchanges heat with TFE circulating through the circulation pipe 43. Next the carbon dioxide passed through the fourth heat exchanger 37 is further supplied to the fifth heat exchanger 38 located downstream and exchanges heat with the water supplied from the second water pipe 39*b* to change the water to hot water having a temperature of 80° C. The carbon dioxide passed through the fifth heat exchanger 38 is circulated to the expansion valve 34 at a pressure of 13 MPa and a temperature of 40° C.

In the meantime, in the circulation pipe 43, a heat medium, i.e., TFE, is first expanded by the expansion valve 46 into a state of a pressure of 0.1 MPa and a temperature of 74° C., and then supplied to the fourth heat exchanger 37. As a result, the TFE exchanges heat with the carbon dioxide circulated through the circulation pipe 33 at the fourth heat exchanger 37 and increases in temperature to about 100° C.

Next, the TFE passed through the fourth heat exchanger 37 is supplied to the compressor 44 and compressed therein into a state of a pressure of 0.83 MPa and a temperature of 165° C., and then supplied to the sixth heat exchanger 45. Subsequently, at the sixth heat exchanger 45, the TFE exchanges heat with hot water having a temperature of 80° C. and taken out from the secondary side of the fifth heat exchanger 38 and supplied through the hot water pipe 47 to change the hot water into water vapor having a temperature of 130° C. The TFE passed through the sixth heat exchanger 45 (in the state where a pressure is 0.83 MPa and a temperature is 100° C.) is circulated to the expansion valve 46.

The water vapor having a temperature of 130° C. obtained in the sixth heat exchanger 45 is supplied to the slurry pipe 11 through the vapor pipe 15 and used for reheating the slurry.

Reference Signs List

1 . . . Lignocellulosic biomass saccharification pre-treatment device, 2 . . . Mixer, 3 . . . First multitubular heat exchanger, 4 . . . Separation tower, 5 . . . Later process, 6 . . . Transfer pipe, 8 . . . Ammonia water supply pipe, 11 . . . Slurry pipe, 13 . . . Hold tank, 15 . . . Vapor pipe, 19 . . . First heat exchanger, 20 . . . Recovery Tower, 24 . . . The second heat exchanger, 27 . . . Second multitubular heat exchanger, 30 . . . Heat pump, 33 . . . Circulation pipe, 35, 35*a* . . . The third heat exchanger, 43 . . . Circulation pipe.

The invention claimed is:

1. A lignocellulosic biomass saccharification pre-treatment device comprising:

a mixing unit which mixes lignocellulosic biomass and ammonia, a heating unit which heats a biomass-ammonia mixture obtained by the mixing unit, a separation unit which separates ammonia gas from the biomass-ammonia mixture heated by the heating unit to obtain a biomass-water mixture, and a transfer unit which transfers the biomass-water mixture separated by the separation unit to a later process, wherein the device comprises an ammonia water supply unit which supplies ammonia water to the mixing unit, an ammonia recovery unit which recovers ammonia gas separated by the separation unit as ammonia water by dissolving the ammonia gas in water, a heat-of-dissolution recovery unit which recovers heat-of dissolution generated when ammonia gas is dissolved in water by the ammonia recovery unit, and a heat pump unit which generates heat to be supplied to the heating unit by using at least the heat-of-dissolution recovered by the heat-of-dissolution recovery unit as a heat source.

2. The lignocellulosic biomass saccharification pre-treatment device according to claim 1, comprising a reheating unit which reheats the biomass-ammonia mixture heated by the heating unit and an evaporating unit which evaporating ammonia gas from the biomass-ammonia mixture heated by the reheating unit between the heating unit and the separation unit.

3. The lignocellulosic biomass saccharification pre-treatment device according to claim 2, comprising a first heat recovery unit which recovers heat from ammonia gas separated by the separation unit and a second heat recovery unit which recovers heat from the biomass-water mixture separated by the separation unit, wherein the heat pump unit generates heat to be supplied to the heating unit and the reheating unit using the heat-of-dissolution recovered by the heat-of-dissolution recovery unit and the heat recovered by the first and second heat recovery unit as a heat source.

4. The lignocellulosic biomass saccharification pre-treatment device according to claim 2, comprising a third heat recovery unit which recovers heat in the air, wherein the heat pump unit has a first heat pump for generating heat to be supplied to the heating unit using heat-of-dissolution recovered by the heat-of-dissolution recovery unit and heat recovered by the third heat recovery unit as a heat source and a second heat pump for generating heat to be supplied to the reheating unit using the heat generated by the first heat pump as a heat source.

5. The lignocellulosic biomass saccharification pre-treatment device according to claim 1, comprising a storage unit which stores the biomass-ammonia mixture heated by the heating unit.

* * * * *